United States Patent [19]

Larimore

[11] 4,394,904

[45] Jul. 26, 1983

[54] PERIPHERALLY SUPPORTED PACKAGE FOR ADHESIVE-SURFACED ARTICLES

[75] Inventor: Franklin C. Larimore, Shoreview, Minn.

[73] Assignee: Minnesota Mining and Manufacturing Company, St. Paul, Minn.

[21] Appl. No.: 292,008

[22] Filed: Aug. 11, 1981

Related U.S. Application Data

[63] Continuation-in-part of Ser. No. 224,446, Jan. 12, 1981, abandoned, which is a continuation-in-part of Ser. No. 203,566, Nov. 5, 1980, abandoned.

[51] Int. Cl.$^3$ .............................................. B65D 85/70
[52] U.S. Cl. .................................... 206/447; 206/813; 206/820; 206/824; 206/390
[58] Field of Search ............... 206/447, 225, 38, 390, 206/412, 484, 39.3, 813, 820, 824

[56] References Cited

U.S. PATENT DOCUMENTS

| | | | |
|---|---|---|---|
| 2,424,508 | 7/1947 | Simmonds | 206/447 |
| 2,783,172 | 2/1957 | Avery | 206/447 |
| 2,797,801 | 7/1957 | Bishop, Jr. | 206/447 |
| 2,831,277 | 4/1958 | Strachan | 206/447 |
| 2,883,044 | 4/1959 | Kendrick | 206/447 |
| 3,035,957 | 5/1962 | Morgan | 206/447 |
| 3,191,767 | 6/1965 | Glouiak | 206/447 |
| 4,055,249 | 10/1977 | Kojima | 206/447 |

Primary Examiner—Joseph Man-Fu Moy
Attorney, Agent, or Firm—Cruzan Alexander; Donald M. Sell; Lorraine R. Sherman

[57] ABSTRACT

A package for adhesive-surfaced sheet-like articles which may be delicate is formed by mounting the adhesive surface of the article onto a two-part release-surfaced carrier, one part of which supports the periphery of the article and the other part supporting the interior area of the article. With such a package, adhesive-surfaced sheet-like articles can be accurately placed onto an adherend without danger of contaminating the adhesive surface or allowing tearing, curling, or distortion of the article.

18 Claims, 6 Drawing Figures

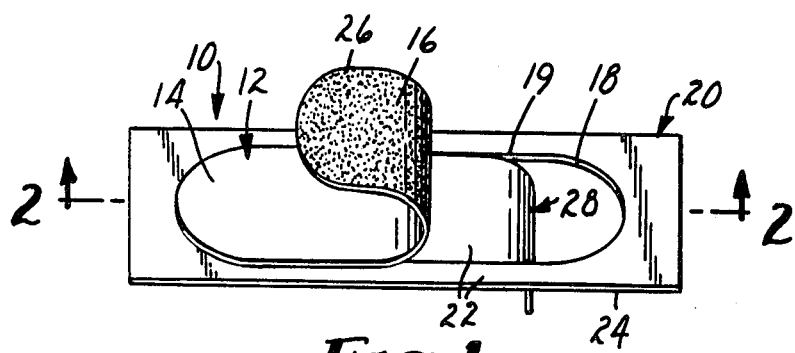
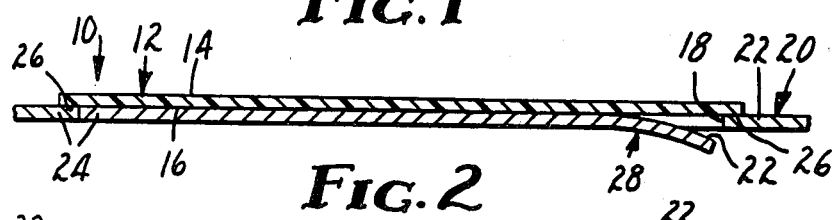
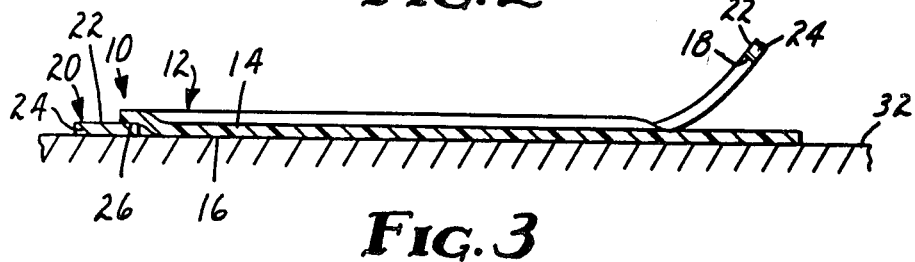
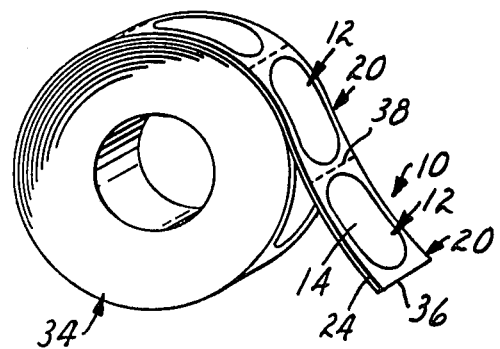

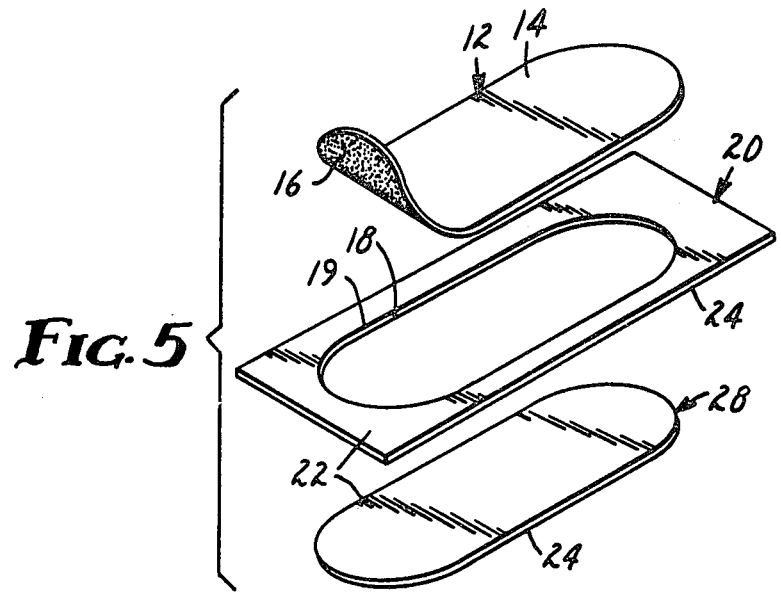
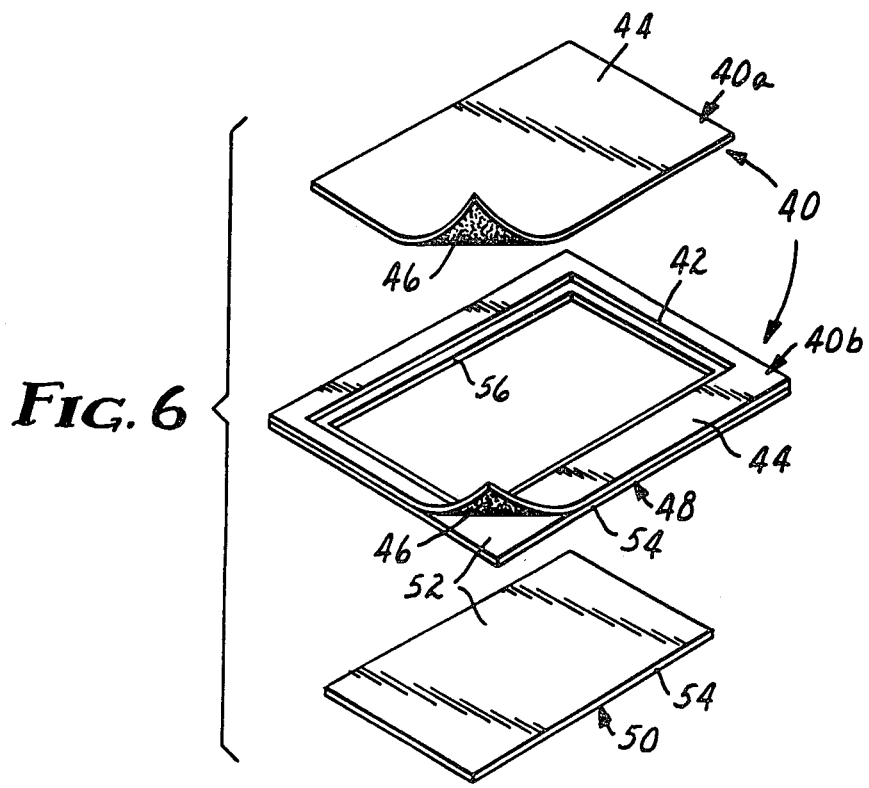

PERIPHERALLY SUPPORTED PACKAGE FOR ADHESIVE-SURFACED ARTICLES

This application is a continuation-in-part of copending application Ser. No. 224,446, filed Jan. 12, 1981, which is a continuation-in-part of copending application Ser. No. 203,566, filed Nov. 5, 1980, now all abandoned.

TECHNICAL FIELD

This invention relates to packaged adhesive-surfaced sheet-like articles. Particularly, this invention relates to packaged, delicate, sheet-like articles and to methods of application of these fragile articles to an adherend.

BACKGROUND ART

It has been customary for many years to mount adhesive-surfaced articles such as bandages, name tags, and transfer decalcomanias onto a release liner from which the article has to be peeled prior to placement at its intended location. Often, it is difficult to separate an edge of the article from the release liner, and even after this is accomplished the article invariably curls up and frequently becomes unmanageable. The placement of such an adhesive-surfaced article after removal from the liner is generally complicated by the difficulty, if not altogether impossibility, of holding the article in such a manner as to avoid contaminating or damaging the adhesive surface.

Articles which can be applied to an adherend without the necessity of touching the surface have been proposed. Thus, it is disclosed in U.S. Pat. No. 2,703,083, among others, that the adhesive surface of the article may have releasably attached thereto a plurality of overlaying protective facing members which have finger gripping portions by which the facing members may be stripped from the adhesive without touching the adhesive. Although such a packaging construction allows for improved handling and placement of adhesive-surfaced articles, the often different release rates of the various protective facing members makes it difficult to avoid curling, wrinkling, folding, stretching, or surface-contamination of the adhesive-surfaced article during application. Where the adhesive-surfaced article is extremely fragile, this curling, wrinkling, folding, and stretching of the adhesive-surfaced article simply cannot be avoided.

U.S. Pat. No. 3,899,077 discloses another means for packaging an article having adhesive zones. In accordance with this patent, a strip package is provided for a flat adhesive bandage, the bandage having a central pad and adhesive zones on each side thereof, and the adhesive zone being covered by removable protective foils. At least one of the protective foils is automatically removed when the bandage is removed from the strip package. Such a strip package does not provide a means for the handling and placement of fragile, adhesive-surfaced articles so as to avoid curling, wrinkling, and stretching the adhesive-surfaced article.

U.S. Pat. No. 3,260,260 discloses a surgical drape or laminate comprising a flexible plastic sheet with a pressure sensitive adhesive on the center portion of one of its surfaces, a cover sheet releasably attached thereto, and a pair of handles or strips, to provide removal means, attached to marginal portions of the flexible plastic sheet by means of a permanent adhesive. Such a laminate is of limited use as a bandage or decal due to the presence of the permanent pair of handles.

It is known in the art to attach a substantial, adhesive-surfaced sheet-like article to an adherend, the purpose of which is to hold a device, such as a bioelectrode, in position on a living body. This article has an adhesive surface which is covered with a release sheet having a central scored portion for separate removal therefrom. However, much smaller ratios of total article area to apertured release sheet area, and much greater article thickness, are required in the prior art article than are useful in the present invention. In addition, the utility disclosed herein is very different from the prior art usage.

DISCLOSURE OF INVENTION

The present invention provides an adhesive-surfaced article packaged for facile placement onto an adherend without distortion and surface contamination of the article. The package comprises a release carrier sheet having an aperture cut therein and the adhesive-surfaced article, particularly an adhesive-surfaced delicate article, disposed over the aperture and overlapping the periphery of the carrier sheet around the aperture to an extent necessary to support the article. A release cover, either cut out from the release carrier sheet or from a separate release sheet, protects the adhesive surface of the article exposed by the aperture. The release carrier sheet with the aperture cut therein is hereinafter referred to as the peripheral release carrier. The adhesive surface of the carrier can also be protected by placing the articles one on top of the other to form a stack or pad. In this arrangement the upper surface of the article is preferably treated with a low-adhesion backsize to allow separation of the articles. The design of the overlap is significant. The adhesive bond between the article and the peripheral release carrier must be sufficient to support the article during removal of the release cover, yet low enough to allow removal of the peripheral carrier after the article is adhered to the intended surface.

Briefly summarizing, the present invention provides a package comprising:

an adhesive-surfaced, sheet-like article;

a release carrier laminated to the adhesive surface of the article and apertured to form a peripheral release carrier that is releasably adhered to peripheral areas of said adhesive surface; and a release cover, substantially as large or larger than said aperture in said release carrier, releasably adhered over the portion of said adhesive surface exposed by said aperture;

the ratio of the length of a straight line joining any two points on the perimeter of the article and passing through the center of the article, to the summation of the lengths of the segments of that line overlapped by said peripheral release carrier, being at least about 5 to 1.

With such a package, delicate, adhesive-surfaced sheet-like articles such as bandages and decalcomanias which may be fragile can be handled without curling or distortion and accurately placed onto an adherend without danger of contaminating the adhesive surface.

A "delicate" article refers to a thin element which may be flexible, rigid, strong, limp, brittle, filmy or fragile, can be easily torn or hurt, or is subject to stretching, wrinkling, folding or to surface contamination. It is up to 250 microns thick.

The invention further provides a process for placement of an adhesive-surfaced article onto an adherend comprising the steps of packaging the article in the described assembly, removing the release cover from said article, as by flexing the package to release an edge of the release cover and peeling the release cover from the adhesive-surfaced article while holding the peripheral release carrier, positioning the adhesive-surfaced article onto an adherend and adhering it thereto, and removing the peripheral carrier by pulling the release carrier sheet away from the edges of the attached article while the article is in position on the adherend.

Additionally, the invention provides a process for mechanically placing an adhesive-surfaced article onto an adhered comprising the steps of packaging the article in the described assembly, removing the release cover from the article, and then mechanically plucking the article from the peripheral release carrier by means of a vacuum, contact adhesion device, or other suitable instrument which contacts and adheres to the article. Mechanical plucking depends on a difference in relative holding strengths between the plucking means and article, and the article and peripheral release carrier. Successful plucking requires the former strength to be greater than the latter strength. With the release cover removed, the required differential in relative strengths is easily achieved. For example, a vacuum platen can be utilized to contact the top of the article to be plucked, causing the article to adhere to the platen if the vacuum strength is greater than the adhesive strength of the article. Then, mechanically, the platen transfers, positions, and applies the article to the designated adherend. The platen is then removed from the article. A contact adhesive or other suitable device can be similarly used.

BRIEF DESCRIPTION OF DRAWINGS

In the accompanying diagrammatic drawings which illustrate the invention:

FIG. 1 is a perspective view of a packaged adhesive-surfaced bandage according to the present invention;

FIG. 2 is a cross-section of the packaged article shown in FIG. 1 taken along line 2—2, showing the beginning of the removal of the release cover from the package;

FIG. 3 is a cross-section similar to FIG. 2, showing the application of the article onto an adherend;

FIG. 4 is a perspective view of a roll of packages of the invention;

FIG. 5 is an exploded perspective view of a packaged bandage according to the invention; and FIG. 6 is an exploded perspective view of a packaged decalcomania according to the invention.

DETAILED DESCRIPTION OF THE INVENTION

Referring now more particularly to the drawings, FIG. 1 shows a package 10 comprising a delicate, adhesive-surfaced article 12, having upper sheet-like element 14 and pressure sensitive adhesive lower layer 16. The article 12 fits over and is slightly larger in dimensions than an aperture 18 in a release carrier 20, which comprises a release coating 22 on substrate 24 (see FIG. 2). The carrier 20 supports the adhesive-surfaced sheet-like article 12 around the periphery 26 of the article. A portion of the adhesive surface 16 of sheet-like article 12 is exposed by the aperture 18 and this exposed portion is covered by release cover 28. As shown, release cover 28 is cut out of release carrier 20 along cut lines 19 and has the exact dimensions of aperture 18, although it may be a separately applied release cover of dimensions different from those of aperture 18.

FIG. 2 shows the package 10 of FIG. 1 in cross-section. Release cover 28 is beginning to be removed by peeling it away from sheet-like article 12. In preferred usage this peeling is caused by flexing package 10.

FIG. 3 shows, in cross-section, the application of sheet-like article 12 to an adherend 32. Release cover 28 has been removed and adhesive surface 16 of sheet-like article 12 is exposed. Release carrier 20, from which release cover 28 has been removed to form a peripheral release carrier, is readily positioned, without curling or contamination of the sheet-like article 12, on adherend 32. The article 12 is adhered to the adherend 32 by pressure, in the case of a pressure-sensitive adhesive surface 16, or by application of solvent, moisture, or heat when other types of adhesives are used. Release carrier 20, from which release cover 28 has been removed, is gently pulled away from sheet-like article 12 and thereby removed from the periphery 26 of the article, leaving the article in position. Slight additional pressure, solvent, moisture, or heat applied to article 12 along its periphery secures it neatly to adherend 32.

FIG. 4 shows a coil 34 of packages 10 mounted on release carrier 20 which is scored between each package at perforations 38 for easy separation of an individual package 10. Coil 34 may be unwound and separated by passing it under and around a dowell (not shown) having a diameter of about 5 to 25 mm, sufficient to cause the release cover to separate at its kiss cut from the release carrier supporting the article 12. Package 10 may be grasped at end 36 and easily torn or cut (by means not shown) at score 38.

FIG. 5 depicts an exploded view of one embodiment of the present invention. Bandage 12 has sheet-like element 14 and lower adhesive surface 16. Release carrier 20 comprises release coating 22 on substrate 24 and has aperture 18 cut therein. Release cover 28 is created by kiss cutting release carrier 20 along cut lines 19 and has the dimensions of aperture 18 and comprises upper release coating 22 on substrate 24.

FIG. 6 shows an exploded view of another embodiment of the invention. Decalcomania 40a has been kiss cut along cut lines 42 from sheet-like article 40, which comprises sheet-like element 44 and lower adhesive surface 46. In use, peripheral release carrier 48 supports both decal 40a and residual portion 40b of sheet-like article 40. Release cover 50 is kiss cut from the release carrier thereby forming aperture 56. Peripheral release carrier 48 and release cover 50 both have upper release coating 52 on substrate 54.

As mentioned above, adhesive-surfaced article 12 comprises a sheet-like element 14 and a lower adhesive layer 16. Sheet-like element 14 can be any sheet-like body, i.e., an article having relatively small thickness in comparison to its length and breadth. Examples of sheet-like element 14 include bandage constructions, sealing gaskets, validation labels, and decalcomanias. Sheet-like element 14 may comprise one or more layers of woven or nonwoven fibers or plastic sheet material and may be body-fluid absorptive or non-absorptive and, if desired, may carry medication. Particularly useful packages of the invention are embodiments where the sheet-like element is a mechanically fragile decalcomania useful for providing tamper-proof labels for machinery, appliances, and the like. It is also contemplated that the sheet-like element may have a second adhesive layer. In this event, a second release sheet is used over this second adhesive layer and is removed after positioning of the article on the adherend.

Lower adhesive layer 16 preferably is a coating of pressure sensitive adhesive but could instead be any moisture, solvent, or heat activated adhesive coating known in the art. Adhesives that may be used include acrylate-type adhesives as disclosed in U.S. Pat. No. Re. 24,906 and U.S. Pat. No. 4,112,213. Adhesive layer 16 can cover the entire lower surface of the article 12 or it can be applied in a regular or random pattern so that only about 10 to 80 percent of the lower surface of the article is covered.

Release carrier 20 and release cover 28 can be formed from any sheet material, transparent or opaque, to which a releasable bond can be made with adhesive layer 16. Generally, any sheet material to which the adhesive of layer 16 bonds with a peel force of less than about 400 g/cm, as described, for example, in U.S. Pat. No. 4,157,418, is suitable. Examples of such sheet materials include polyethylene, polypropylene, Teflon, silicone resin treated paper, fluorocarbon treated paper, and the like. Examples include NS62 Buff® VBL 251-1 from Akrosil, and paper or film which is first coated with a layer of polyethylene and then overcoated with a silicone release agent, commercially available as Polyslik® SH 8004 from H. P. Smith Co. Other abherent materials are the polyacrylate and polymethacrylate fluorocarbon polymers disclosed in U.S. Pat. No. 2,803,615. Teflon and silicone resins are inherently releasant and do not require a release coating. Release carrier 20 has an aperture or opening 18 cut or punched out of release sheet material, the aperture being made so that a peripheral area of the release carrier of up to 10 mm, preferably about 1 to 5 mm, in width will be overlapped by the article 12; in other words article 12 is slightly larger than aperture 18 in release carrier 20. In some instances it is useful to eliminate the overlap at projections on the article or at the starting point for peeling off the remaining peripheral carrier; a scalloped peripheral edge may be desirable in some cases.

The ratio of the length of a straight line joining any two points on the perimeter of the article and passing through the center of the article, to the summation of the segments of that line overlapped by said peripheral release carrier, should be at least about 5 to 1 to achieve convenient removal of the peripheral release carrier after the sheet-like article has been adhered to an adherend. The article may be of any desired shape, e.g., square, rectangular, circular, oval, or irregular. Where the total area of the article is 50 cm² or less, it is preferable that the aforementioned ratio be at least about 8 to 1.

The package according to the invention is formed preferably by applying the adhesive-surfaced article to release sheet material and then kiss cutting the adhesive-surfaced article to the desired dimensions and, if desired for cosmetic reasons, removing the weed, and kiss cutting an aperture in the release sheet material so that the periphery of the release sheet material around the aperture will be suitably overlapped by the outer edges of the adhesive-surfaced article. Alternately, the release carrier may be non-continuously kiss cut to form alternate cut and uncut segments in the release carrier between packages. The packaged articles can then be separated, stacked and placed in boxes or they can be left unseparated and coiled into rolls for distribution.

By "kiss cutting" is meant the cutting of one layer of a laminate without cutting a lower layer. Kiss cutting can be accomplished by use of a die in a platen or rotary die-cutting press.

An advantage of the package of the invention is the inherent characteristic of the automatic separation of the release cover from the adhesive-surfaced sheet-like article on flexing the package. This procedure was described above in the discussion of FIG. 4. In addition, the delicate sheet-like article of the present invention may be readily positioned onto an adherend without curling or stretching, and without touching the adhesive coated thereon.

Various modifications and alterations of this invention will become apparent to those skilled in the art without departing from the scope and spirit of this invention, and it should be understood that this invention is not to be unduly limited to the illustrative embodiment set forth herein.

What is claimed is:

1. A package comprising:
  (a) an adhesive-surfaced, delicate sheet-like article;
  (b) a release sheet laminated to the adhesive surface of said article and cut to form
    (1) a peripheral release carrier that is releasably adhered to peripheral areas of said adhesive surface and that has a central aperture exposing a major portion of the adhesive surface of said article; and
    (2) a release cover cut out of said release sheet and having the exact dimensions of said aperture in said peripheral release carrier, releasably adhered over the portion of said adhesive surface exposed by said aperture;

the ratio of the length of a straight line joining any two points on the perimeter of said article and passing through the center of said article, to the summation of the segments of that line overlapped by said peripheral release carrier, being at least about 5 to 1.

2. The package according to claim 1 wherein said adhesive-surfaced article overlaps said peripheral release carrier by at most 10 mm.

3. The package according to claim 1 wherein said adhesive-surfaced article overlaps said peripheral release carrier by at most 5 mm.

4. The package according to claim 1 wherein said sheet-like article is up to 250 microns thick.

5. The article according to claim 1 wherein the area enclosed by the outer edge of the adhesive-surfaced article is smaller than the area enclosed by the outer edge of the release carrier.

6. The article according to claim 1 wherein the area enclosed by the outer edge of the adhesive-surfaced article is the same as the area enclosed by the outer edge of the release carrier.

7. The package according to claim 1 wherein the adhesive providing said adhesive surface is a pressure sensitive adhesive.

8. The packaged article according to claim 1 wherein said release carrier is transparent.

9. The package according to claim 1 wherein said article is a delicate article.

10. The package according to claim 1 wherein said article is a fragile article.

11. The package according to claim 1 wherein said sheet-like article is a bandage.

12. The package according to claim 1 wherein said sheet-like article is a decalcomania.

13. The package according to claim 1 wherein said adhesive-surfaced sheet-like article has a second adhesive surface.

14. The package according to claim 1 wherein the entire periphery of said article is supported on every edge by said peripheral release carrier.

15. A roll of packages of the adhesive-surfaced sheet-like articles according to claim 1 wherein said articles are mounted on a release carrier which is perforated between each package.

16. A package comprising two or more sheet-like article according to claim 1: said articles being stacked one upon the other so that an underlying sheet-like article covers the adhesive surface of the overlying article which is exposed by the aperture in its release carrier.

17. The package according to claim 16 wherein the bottom-most article further comprises a release cover releasably adhered to and substantially covering the portion of the adhesive surface of said adhesive-surfaced sheet-like article exposed by said aperture.

18. A package comprising:
 (a) an adhesive-surfaced, delicate sheet-like article;
 (b) a release sheet laminated to the adhesive surface of the sheet-like article and cut to form
   (1) a peripheral release carrier that is releasably adhered to peripheral areas of said adhesive surface and that has a central aperture exposing a major portion of the adhesive surface of said article; and
   (2) a release cover cut out of said release sheet and having the exact dimensions of said aperture in said peripheral release carrier, releasably adhered to and covering the portion of said adhesive surface exposed by said aperture;
said adhesive-surfaced article overlapping said peripheral release carrier by at most 10 mm.

* * * * *